United States Patent [19]

Olejnik

[11] Patent Number: 4,645,768

[45] Date of Patent: Feb. 24, 1987

[54] FORMULATIONS

[75] Inventor: Orest Olejnik, Gatley, England

[73] Assignee: Fisons plc, Ipswich, England

[21] Appl. No.: 754,205

[22] Filed: Jul. 11, 1985

Related U.S. Application Data

[63] Continuation of Ser. No. 571,204, Jan. 16, 1984, abandoned.

[30] Foreign Application Priority Data

Jan. 21, 1983 [GB] United Kingdom ............... 8301754

[51] Int. Cl.$^4$ ..................... A61K 31/330; C07C 87/28
[52] U.S. Cl. .................................... 514/649; 564/367
[58] Field of Search .......................... 514/649; 564/367

[56] References Cited

U.S. PATENT DOCUMENTS

| | | | |
|---|---|---|---|
| 2,653,977 | 9/1953 | Craig et al. | 564/367 |
| 3,969,410 | 7/1976 | Mentrup et al. | 514/649 |
| 4,010,282 | 3/1977 | Binnig et al. | 514/649 |

FOREIGN PATENT DOCUMENTS

| | | | |
|---|---|---|---|
| 0791745 | 3/1958 | United Kingdom | 564/367 |
| 0987435 | 3/1965 | United Kingdom | 564/367 |

OTHER PUBLICATIONS

"Remington's Phar. Sciences" 16th Ed., pp. 1432–1433 and 1483–1484 (1980).

*Primary Examiner*—Donald B. Moyer
*Assistant Examiner*—John W. Rollins, Jr.
*Attorney, Agent, or Firm*—Marshall, O'Toole, Gerstein, Murray & Bicknell

[57] ABSTRACT

There is described a mixture of 4-[2-(6-(2-phenylethylamino)hexylamino)ethyl]-1,2-benzenediol, or 4-[2-(6-(2-chlorophenyl)ethylamino)hexylamino)ethyl]-1,2-benzenediol or a pharmaceutically acceptable acid addition salt of either thereof or as active ingredient, and a physiologically acceptable acid.

There is also described a method of preparing a solid form of the active ingredient, which comprises freeze drying an aqueous solution of the mixture, and a freeze dried composition containing the active ingredient prepared by the method.

The mixtures are useful as pharmaceuticals, e.g. in the treatment of cardiovascular conditions.

5 Claims, No Drawings

FORMULATIONS

This application is a continuation, of application Ser. No. 571,204, filed 1/16/84 now abandoned.

This invention relates to a new formulation and to a method for its preparation.

According to the invention we provide a mixture of 4-[2-(6-(2-phenylethylamino)hexylamino)-ethyl]-1,2-benzenediol, or 4-[2-(6-(2-(4-chlorophenyl)ethylamino) hexylamino)-ethyl]-1,2-benzenediol, or a pharmaceutically acceptable acid addition salt of either thereof as active ingredient, and a physiologically acceptable acid.

We prefer the active ingredient to be in the form of an acid addition salt. Suitable salts include salts of mineral acids, for example, hydrohalic acids, e.g. hydrochloric acid or hydrobromic acid, or organic acids, e.g. formic, acetic or lactic acids. The acid may be polybasic, for example sulphuric, fumaric or citric acid. We also prefer the mixture to include the first named active ingredient.

The active ingredients may be made by the methods described in Examples 1 and 2. Salts other than those described in Examples 1 and 2 may be made from the salts disclosed in Examples 1 or 2, or from the free bases using conventional techniques, e.g. ion-exchange chromatography.

The mixture of the active ingredient and the acid may be solid, or may be in solution.

The solution is preferably an aqueous solution and preferably has a pH of less than 3.5 and more preferably less than 3.0. The solution also preferably has a pH of greater than 1.5 and more preferably of greater than 2. We particularly prefer the solution to have a pH of from 2 to 3, e.g. of about 2.5.

We have surprisingly found that acidic solutions of the active ingredient are more stable than are neutral or basic solutions.

We prefer the solution to be substantially free of dissolved oxygen. We also prefer the solution to be substantially free of metal ions, other than those of group Ia of the periodic table. We particularly prefer the solution to be substantially free of transition metal ions, especially copper, chromium and iron. By substantially free, we mean less than 20 ppm, preferably less than 10 ppm, and particularly less than 5 ppm of the metal ions.

The solutions described immediately above are, in general, too acidic for direct administration to the body, but may be suitably diluted, e.g. with water for injection, or isotonic saline to give solutions of a physiologically acceptable pH, e.g. with a pH of from 4 to 8.

The concentration of the active ingredient in the solution will vary with the active ingredient and with the particular salt used. However we prefer a concentration of active ingredient (determined as hydrochloride salt) of from 0.5 to, 10%, e.g. of from 1.0 to 5.0% and especially of about 2.0% w/v.

The concentration of the acid in the solution will be such as to give the desired pH.

The physiologically acceptable acid may be any suitable organic or inorganic acid. The acids are preferably suitable for administration by injection or infusion. Acids which may be mentioned include hydrochloric, ascorbic, tartaric, malic, maleic, and citric acid.

A solution containing a mixture of an active ingredient and a physiologically acceptable acid may, if desired, be evaporated, e.g. by freeze drying or spray drying, to give a solid composition. Preferably the solution is sterile filtered and/or autoclaved prior to evaporation. Solid compositions are advantageous in that they do not require the transport of large volumes of water, and that they may be made up immediately before use.

Surprisingly we have found that aqueous solutions of mixtures according to the invention may be freeze dried to give a solid composition containing fewer degradation products of the active ingredient than is obtained by freeze drying neutral or basic solutions of the active ingredient.

Accordingly, we provide a method of preparing a solid form of an active ingredient as hereinbefore defined which comprises freeze drying an aqueous solution of a mixture as hereinbefore defined.

The solution for evaporation may contain a volatile acid, e.g. hydrochloric acid or a non-volatile acid, e.g. ascorbic acid. The solid composition produced by evaporation may be reconstituted, e.g. with sterile, isotonic saline or with water for injection. Such reconstituted solutions may, if necessary, be buffered at a pH suitable for direct intravenous infusion, e.g. at a pH from 4 to 8, particularly 4.5 to 7.5, or at a pH of between 1.5 and 3.5, for subsequent dilution with e.g. isotonic saline. Alternatively, when the acid is non-volatile the solid composition may be reconstituted by adding an appropriate quantity of water, preferably sterile demineralised water, to provide an aqueous solution approximately corresponding in pH to the original solution.

Reconstitutable solid compositions, prepared by evaporating solutions containing a mixture according to the invention may be packed in suitably adapted pharmaceutical application devices, e.g. syringes, infusion bags or ampoules, such that addition of sterile isotonic saline solution allows in situ preparation of an aqueous solution of active ingredient in a form suitable for immediate administration to a patient.

The mixtures, and in particular the aqueous formulations, may contain other excipients in addition to the active ingredient and the acid. In particular there may be mentioned antioxidants, e.g. sodium metabisulphite; chelating agents, e.g. mono- or di-sodium edetate; sodium chloride; and buffering agents, e.g. sodium citrate. We prefer to avoid the use of phosphate buffers as these have been found to enhance degradation of the active ingredients in aqueous solution. The solution may also, if desired, contain a reducing sugar, e.g. dextrose. When the solution containing the mixture is intended for evaporation to a reconstitutable powder, the solution may also contain a physiologically acceptable inert filler, e.g. mannitol.

The mixtures of the invention may be made by dissolving the active ingredient and any excipients in water, preferably deoxygenated water, and adjusting the pH to the desired value by addition of the preferred acid or mixture of acids. The solution may be sterilised, e.g. by filtration, or by autoclaving, and then if desired, evaporating, e.g. freeze drying, using conventional techniques, to give a solid. The solid mixture may be reconstituted, e.g. with deoxygenated water or water for injection, BP, as required, to give solution formulations of the mixtures.

When the components of the mixture are non-volatile solids, e.g. when the acid is ascorbic acid and the active ingredient is a hydrochloride salt, the mixture may be prepared by mixing, e.g. comminuting, the components.

The mixtures may be stored as solutions or as a solid composition. We prefer to store the solution mixtures in neutral glass ampoules which have been surface treated in order to reduce contamination by metal ions. A particularly suitable treatment procedure is to wash the ampoule first with aqueous acid solution, followed by washing with 3% w/v aqueous ammonium sulphate solution. Alternatively the ampoules may be washed with an acidified ammonium sulphate solution. Solid mixtures are preferably stored in neutral glass vials.

We prefer aqueous formulations of the mixture to be sealed in surface treated ampoules of from 0.5 to 25 ml preferably 1 to 10 ml, particularly 2 to 5 ml. We especially prefer a 2% w/v aqueous formulation of the active ingredient to be sealed in an ampoule of between 1 and 10 ml capacity, e.g. in 2 or 5 ml ampoules. The ampoules are preferably filled under nitrogen.

The mixtures are preferably stored at ambient temperature and protected from light.

According to the invention, we also provide a unit pack containing the mixture as hereinbefore defined wherein the pack contains from 10 to 500 mg (determined as the dihydrochloride salt) of an active ingredient according to the invention.

The active ingredients are useful because they possess pharmacological activity in animals. Thus the compounds act on peripheral and/or central dopamine receptors. As such, they lower blood pressure, reduce heart rate and increase blood flow to certain vascular beds, e.g. renal beds. The compounds also have an action on other adrenoreceptors, and exhibit cardiac stimulant and bronchodilator effects. Activity of the compounds has been observed in the following assay systems:

(a) canine renal blood flow, McNay and Goldberg, J. Pharmac, Exp. Ther., 151, 23–31, 1966.
(b) rabbit isolated ear artery, McCullogh, Rand and Story, Br. J. Pharmac, 49, 141–142, 1973, and
(c) cat nictitating membrane, Gyorgy and Doda, Arch. Int. Pharmacodyn, 226, 194–206, 1977.

The compounds are indicated for use in the treatment of congestive heart failure, renal failure, angina pectoris, ischaemic heart disease, hypertension and reversible obstructive airways disease, hyperprolactinaemia and also in Parkinson's disease and other neurological disorders.

The dosage administered will naturally depend on the active ingredient employed, the mode of administration and the desired effect. However, in general, satisfactory results are obtained when the compounds are administered at a dosage of from 0.05 $\mu$g to 50 mg per kilogram of body weight per day. For man, the indicated total daily dosage is in the range 2.5 $\mu$g to 3.5 g, which may be administered in divided doses of, for example 1 $\mu$g to 750 mg.

The active ingredients have the advantage that they are more efficacious or produce less undesirable side effects in certain pharmacological models, or are longer acting than compounds of similar structure.

The mixtures of the invention may be administered by a wide variety of routes and may act systemically or locally. Thus the compounds may be administered by oral or nasal inhalation to the lung, to the buccal cavity, oesophageally, rectally, topically to the skin or to other available surfaces of the body, but are preferably administered as solutions by infusion, e.g. intravenously.

When the active ingredient is administered by intravenous infusion, the indicated infusion rate for man is in the range of 0.1 to 20, preferably 0.5 to 10 $\mu$g active ingredient (determined as hydrochloride salt)/kilogram of body weight/minute. The active ingredient may be administered continuously or intermittently as required, for periods of, e.g. 0.5 to 48 hours.

According to the invention, we further provide a method of increasing the force of contraction of the heart in an animal, either human or non-human, which method comprises administering to the animal an effective amount of a mixture of the invention.

The invention is illustrated, but in no way limited by the following examples. All temperatures quoted are in °C.

EXAMPLE 1

4-[2-(6-(2-Phenylethylamino)hexylamino)ethyl]-1,2-benzenediol (a)

N-[2-(3,4-Dimethoxyphenyl)ethyl]-N'-[2-phenylethyl]-hexane-1,6-diamide

A solution of 6-oxo-6-(2-(3,4-dimethoxyphenyl)ethylaminohexanoic acid (9.3 g), and N,N'-carbonyldiimidazole (4.90 g) in dry dichloromethane (300 ml) was stirred at room temperature for 2 hours. A solution of 2-phenylethylamine (3.8 ml) in dichloromethane (50 ml) was added and the mixture stirred at room temperature for 3 hours.

The solution was washed with 2N HCl, water, 5% aqueous sodium bicarbonate solution and water. The organic phase was dried over magnesium sulphate, filtered and evaporated to leave a solid which crystallized from ethanol (11.38 g), m.p. 183°–184°.

(b)

N-[2-(3,4-Dimethoxyphenyl)ethyl]-N'-[2-phenylethyl]-hexane-1,6-diamine dihydrochloride A solution of the diamide product of step 1 (a) (4.94 g) in dry tetrahydrofuran (150 ml) was stirred under a nitrogen atmosphere while diborane in tetrahydrofuran (48 ml of 1 M solution) was added. The solution was heated under reflux for 24 hours.

Methanol (100 ml) was added to the cooled solution and the mixture evaporated to dryness. The residue was dissolved in methanolic HCl (100 ml) and heated under reflux for 1 hour. The solution was evaporated and the solid crystallised from methanol (4.90 g), mp 283°–285°.

(c)

4-[2-(6-(2-Phenylethylamino)hexylamino)ethyl]-1,2-benzenediol dihydrobromide

A solution of the diamine product of step (b) (4.75 g) in 48% aqueous hydrobromic acid (70 ml) was heated under reflux in an atmosphere of nitrogen for 3.5 hours. The solid which formed on cooling was filtered off and crystallised from ethanol, to give the title compound as the dihydrobromide salt, (3.1 g), mp 227°–228°.

EXAMPLE 2

4-[2-(6-(2-(4-Chlorophenyl)ethylamino)hexylamino)ethyl]-1,2-benzenediol (a)

N-[2-(3,4-Dimethoxyphenyl)ethyl]-N'-[2-(4-chlorophenyl)ethyl]-hexane-1,6-diamide The sub-title compound was prepared using the method of Example 1(a), mp 167°–169°.

(b)
N-[2-(3,4-Dimethoxyphenyl)ethyl]-N'-[2-(4-chlorophenyl)ethyl]-hexane-1,6-diamine The sub-title compound was prepared using the method of Example 1(b), mp 260°.

(c)
4-[2-(6-(2-4-Chlorophenyl)ethylamino)hexylamino)ethyl]-1,2-benzenediol dihydrobromide The title compound was prepared, as the dihydrobromide salt, using the method of Example 1(c), mp 172°–174°.

EXAMPLE 3

4-[2-[6-[2-(4-Chlorophenyl)ethylamino]hexylamino]ethyl]-1,2-benzenediol dihydrochloride 4-[2-[6-[2-(4-Chlorophenyl)-ethylamino]hexylamino]ethyl]-1,2-benzenediol dihydrobromide (3.0 g) was dissolved in the minimum amount of water and saturated sodium bicarbonate was added until the pH of the solution was about 8. The precipitated free base was washed with ice cold water and then suspended in concentrated hydrochloric acid and stirred with gentle warming until all the sticky material had been replaced by a fine white solid. The suspension was cooled in ice and filtered and the precipitate recrystallised from ethanol to give the title dihydrochloride (2.0 g) as white crystals mp 186°–188°.

Found Cl: 23.02%, dihydrochloride requires Cl: 22.93%.

EXAMPLE 4

4-[2-[6-(2-Phenylethylamino)hexylamino]ethyl]-1,2-benzenediol dihydrochloride

The title compound was prepared from the corresponding dihydrobromide salt by the method of Example 3, mp 219°–219.5°.

EXAMPLE A

Intravenous Formulations

Demineralised, pyrogen free water is deoxygenated with nitrogen, and added to the active ingredient and excipients. Sufficient acid is added to the solution to give the desired pH, the solution sterile filled in 2 or 5 ml surface treated neutral glass ampoules under nitrogen. The ampoules are then sealed, and stored at ambient temperature protected from the light. As an alternative to sterile filtering, sealed ampoules can be autoclaved for the equivalent of 15 minutes at 121° C.

The ampoules are surface treated by washing with 3% w/v ammonium sulphate acidified to pH 2 with 6M hydrochloric acid.

|  | % w/v |
| --- | --- |
| Formulation 1 | |
| Compound of Example 4 | 2.0 |
| Disodium edetate | 0.01 |
| 6M Hydrochloric acid | qs to pH 2.5 |
| Water | to 100 |
| Formulation 2 | |
| Compound of Example 3 | 2.0 |
| Disodium edetate | 0.01 |
| 6M Hydrochloric acid | qs to pH 2.5 |
| Water | to 100 |
| Formulation 3 | |
| Compound of Example 4 | 2.0 |
| Disodium edetate | 0.01 |
| Dextrose | 5.0 |
| 6M Hydrochloric acid | qs to pH 2.5 |
| Water | to 100 |
| Formulation 4 | |
| Compound of Example 4 | 2.0 |
| Sodium metabisulphite | 1.0 |
| Dextrose | up to 5.0 |
| 6M Hydrochloric acid | qs to pH 2.5 |
| Water | to 100 |

Formulation 4 is preferably sterile filled directly into ampoules or autoclaved in ampoules.

Freeze Dried Formulations

Aqueous solutions of the mixture are prepared as described immediately above. The solution is then sterile filtered and freeze dried, to give a solid composition. The solid composition may be packed in sealed containers, e.g. a crimped container provided with a septum, or a suitably adapted syringe pack or infusion bag.

|  | % w/v |
| --- | --- |
| Formulation 5 | |
| Solution for freeze drying: | |
| Compound of Example 4 | 2.0 |
| Mannitol | 3.0 |
| Disodium edetate | 0.01 |
| 6M Hydrochloric acid | qs to pH 3.0 |
| Water | to 100 |
| Freeze-drying gives a solid with composition: | |
| Compound of Example 4 | 39.92% w/w |
| Mannitol | 59.88% w/w |
| disodium edetate | 0.20% w/w |
| Formulation 6 | |
| Solution for freeze drying: | |
| Compound of Example 4 | 2.0 |
| Ascorbic acid | 0.2 |
| Water | to 100 |
| Freeze-drying gives a solid with composition: | |
| Compound of Example 4 | 90.91% w/w |
| Ascorbic acid | 9.09% w/w |

I claim:

1. An aqueous solution containing 0.5% to 10% w/v of 4-(2-(6-[2-phenylethylamino)hexylamino)-ethyl]-1,2-benzenediol, or 4-[2-(6-(2-(4-chlorophenyl)ethylamino)-hexylamino)-ethyl]-1,2-benzenediol, or a pharmaceutically acceptable acid addition salt of either thereof as active ingredient, and a physiologically acceptable acid, the solution having a pH greater than 1.5 and less than 3.5.

2. A solution according to claim 1, wherein the active ingredient is in the form of an acid addition salt.

3. A solution according to claim 1, wherein the active ingredient is 4-[2-(6-(2-phenylethylamino)hexylamino)ethyl]-1,2-benzenediol dihydrochloride.

4. A method of treatment of congestive heart failure, which comprises administration by intravenous infusion of a solution according to claim 1, suitably diluted to a physiologically acceptable pH, in an amount to provide from 0.5 to 20 μg of active ingredient measured as the hydrochloride salt per kilogram of body weight per minute to a patient suffering from such a condition.

5. A method of treatment according to claim 4, which comprises administration by intravenous infusion for from 0.5 to 48 hours.

* * * * *